US012797123B2

(12) United States Patent
Valls et al.

(10) Patent No.: US 12,797,123 B2
(45) **Date of Patent: *Nov. 17, 2026**

(54) MEDICAL PROBE WITH WIRING DISPOSED BETWEEN TWO EXPANDABLE MEMBRANES

(71) Applicant: Biosense Webster (Israel) Ltd., Yokneam (IL)

(72) Inventors: Jace P. Valls, San Jose, CA (US); Diana S. Gallardo, Wildomar, CA (US); Charles E. Perkins, Danvers, MA (US); Don Q. Ngo-Chu, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 558 days.

This patent is subject to a terminal disclaimer.

(21) Appl. No.: 18/348,120

(22) Filed: Jul. 6, 2023

(65) Prior Publication Data

US 2023/0346471 A1 Nov. 2, 2023

Related U.S. Application Data

(63) Continuation of application No. 16/657,319, filed on Oct. 18, 2019, now Pat. No. 11,717,344.
(Continued)

(51) Int. Cl.

| | |
|---|---|
| *A61B 18/14* | (2006.01) |
| *A61B 18/00* | (2006.01) |

(Continued)

(52) U.S. Cl.
CPC ...... *A61B 18/1492* (2013.01); *A61B 18/1485* (2013.01); *A61B 2018/0022* (2013.01);
(Continued)

(58) Field of Classification Search
CPC ............ A61B 1/00082; A61B 18/0016; A61B 2018/00214; A61B 2018/0022;
(Continued)

(56) References Cited

U.S. PATENT DOCUMENTS

| | | |
|---|---|---|
| D123,782 S | 12/1940 | Paul |
| 3,316,896 A | 5/1967 | Louis |

(Continued)

FOREIGN PATENT DOCUMENTS

| | | |
|---|---|---|
| CN | 101422637 A | 5/2009 |
| CN | 102271607 A | 12/2011 |

(Continued)

OTHER PUBLICATIONS

Extended European Search Report dated Apr. 2, 2020, from corresponding European Application No. 19209784.8.

(Continued)

*Primary Examiner* — Jaymi E Della

(57) ABSTRACT

Shown and described is electrophysiology catheter end effector having a balloon with three expandable membranes attached to each other such that wiring (for the electrodes or other sensors on the membrane surfaces) no longer extend from inside the first membrane yet at the same time is captured between the first membrane and a second membrane.

17 Claims, 5 Drawing Sheets

Related U.S. Application Data

(60) Provisional application No. 62/769,424, filed on Nov. 19, 2018.

(51) Int. Cl.
*A61B 90/00* (2016.01)
*A61M 25/10* (2013.01)

(52) U.S. Cl.
CPC ............... *A61B 2018/00577* (2013.01); *A61B 2018/00791* (2013.01); *A61B 2018/1405* (2013.01); *A61B 2090/3966* (2016.02); *A61M 2025/1043* (2013.01)

(58) Field of Classification Search
CPC ........... A61B 2018/00238; A61B 2018/00285; A61B 2018/00577; A61B 2018/002; A61B 2562/164; A61B 5/6853; A61M 25/10–2025/1097
See application file for complete search history.

(56) References Cited

U.S. PATENT DOCUMENTS 4,276,874 A 7/1981 Wolvek et al.
4,587,975 A 5/1986 Salo et al.
4,709,698 A * 12/1987 Johnston ............ A61B 18/1492 606/41
4,805,621 A 2/1989 Heinze et al.
5,178,957 A 1/1993 Kolpe et al.
5,429,617 A 7/1995 Hammersmark et al.
5,582,609 A 12/1996 Swanson et al.
5,584,830 A 12/1996 Ladd et al.
5,702,386 A 12/1997 Stern et al.
5,718,241 A 2/1998 Ben-Haim et al.
5,797,903 A 8/1998 Swanson et al.
5,860,974 A 1/1999 Abele
5,971,983 A 10/1999 Lesh
6,012,457 A 1/2000 Lesh
6,024,740 A 2/2000 Lesh et al.
6,042,580 A 3/2000 Simpson
6,123,718 A 9/2000 Tu et al.
6,164,283 A 12/2000 Lesh
6,171,275 B1 1/2001 Webster, Jr.
6,176,832 B1 1/2001 Habu et al.
6,198,974 B1 3/2001 Webster, Jr.
6,226,542 B1 5/2001 Reisfeld
6,301,496 B1 10/2001 Reisfeld
6,322,558 B1 11/2001 Taylor et al.
6,380,957 B1 4/2002 Banning
6,402,740 B1 6/2002 Ellis et al.
D462,389 S 9/2002 Provence et al.
6,471,693 B1 10/2002 Carroll et al.
6,522,930 B1 2/2003 Schaer et al.
6,656,174 B1 12/2003 Hegde et al.
6,814,733 B2 11/2004 Schwartz et al.
6,893,433 B2 5/2005 Lentz
6,986,744 B1 1/2006 Krivitski
6,987,995 B2 1/2006 Drysen
6,997,924 B2 2/2006 Schwartz et al.
7,142,903 B2 11/2006 Rodriguez et al.
7,156,816 B2 1/2007 Schwartz et al.
7,274,957 B2 9/2007 Drysen
7,340,307 B2 3/2008 Maguire et al.
7,377,906 B2 5/2008 Selkee
7,442,190 B2 10/2008 Abbound et al.
7,536,218 B2 5/2009 Govari et al.
7,591,799 B2 9/2009 Selkee
7,593,760 B2 9/2009 Rodriguez et al.
7,720,517 B2 5/2010 Drysen
7,756,576 B2 7/2010 Levin
7,842,031 B2 11/2010 Abboud et al.
7,853,302 B2 12/2010 Rodriguez et al.
8,000,765 B2 8/2011 Rodriguez et al.
8,021,327 B2 9/2011 Selkee
8,048,032 B2 11/2011 Root et al.
8,231,617 B2 7/2012 Satake
8,267,932 B2 9/2012 Baxter et al.
8,275,440 B2 9/2012 Rodriguez et al.
8,348,888 B2 1/2013 Selkee
8,357,152 B2 1/2013 Govari et al.
D682,289 S 5/2013 DiJulio et al.
D682,291 S 5/2013 Baek et al.
D690,318 S 9/2013 Kluttz et al.
8,594,705 B2 11/2013 Osann, Jr.
D694,652 S 12/2013 Tompkin
8,641,709 B2 2/2014 Sauvageau et al.
8,721,590 B2 5/2014 Seward et al.
8,777,161 B2 7/2014 Pollock et al.
D716,340 S 10/2014 Bresin et al.
8,852,181 B2 10/2014 Malecki et al.
D720,766 S 1/2015 Mandal et al.
D721,379 S 1/2015 Moon et al.
D724,618 S 3/2015 Shin
8,998,893 B2 4/2015 Avitall
D729,263 S 5/2015 Ahn et al.
9,089,350 B2 7/2015 Willard
D736,780 S 8/2015 Wang
9,126,023 B1 9/2015 Sahatjian et al.
D740,308 S 10/2015 Kim et al.
D743,424 S 11/2015 Danielyan et al.
D744,000 S 11/2015 Villamor et al.
9,173,758 B2 11/2015 Brister et al.
D747,742 S 1/2016 Fan et al.
D750,644 S 3/2016 Bhutani et al.
9,283,034 B2 3/2016 Katoh et al.
9,289,141 B2 3/2016 Lowery et al.
D753,690 S 4/2016 Vazquez et al.
9,320,631 B2 4/2016 Moore et al.
9,345,540 B2 5/2016 Mallin et al.
D759,673 S 6/2016 Looney et al.
D759,675 S 6/2016 Looney et al.
D764,500 S 8/2016 Wang
D765,709 S 9/2016 Gagnier
D767,616 S 9/2016 Jones et al.
D768,696 S 10/2016 Gagnier
D783,037 S 4/2017 Hariharan et al.
9,655,677 B2 5/2017 Salahieh et al.
D791,805 S 7/2017 Segars
9,795,442 B2 10/2017 Salahieh et al.
9,907,610 B2 3/2018 Beeckler et al.
9,956,035 B2 5/2018 Govari et al.
D861,717 S 10/2019 Brekke et al.
10,688,278 B2 6/2020 Beeckler et al.
10,945,786 B2 3/2021 Willard et al.
2001/0031961 A1 10/2001 Hooven
2002/0002369 A1 1/2002 Hood
2002/0065455 A1 5/2002 Ben-Haim et al.
2002/0068931 A1 6/2002 Wong et al.
2002/0077627 A1 6/2002 Johnson et al.
2002/0160134 A1 10/2002 Ogushi et al.
2002/0198521 A1 12/2002 Maguire
2003/0018327 A1 1/2003 Truckai et al.
2003/0028183 A1 2/2003 Sanchez et al.
2003/0050637 A1 3/2003 Maguire et al.
2003/0060820 A1 3/2003 Maguire et al.
2003/0144658 A1 7/2003 Schwartz et al.
2004/0122445 A1 6/2004 Butler et al.
2004/0147920 A1 7/2004 Keidar
2004/0225285 A1 11/2004 Gibson
2005/0070887 A1 3/2005 Taimisto et al.
2005/0119686 A1 6/2005 Clubb
2006/0013595 A1 1/2006 Trezza et al.
2006/0106375 A1 5/2006 Werneth et al.
2006/0135953 A1 6/2006 Kania et al.
2007/0071792 A1 3/2007 Varner et al.
2007/0080322 A1 4/2007 Walba
2007/0083194 A1 4/2007 Kunis et al.
2007/0287994 A1 12/2007 Patel
2008/0018891 A1 1/2008 Hell et al.
2008/0021313 A1 1/2008 Eidenschink et al.
2008/0051707 A1 2/2008 Phan et al.
2008/0140072 A1 6/2008 Stangenes et al.
2008/0183132 A1 7/2008 Davies et al.

(56) References Cited

U.S. PATENT DOCUMENTS

2008/0188912 A1 8/2008 Stone et al.
2008/0202637 A1 8/2008 Hector et al.
2008/0208186 A1 8/2008 Slater
2008/0249463 A1 10/2008 Pappone et al.
2008/0262489 A1 10/2008 Steinke
2008/0281312 A1 11/2008 Werneth et al.
2009/0163890 A1 6/2009 Clifford et al.
2009/0182318 A1 7/2009 Abboud et al.
2009/0270850 A1 10/2009 Zhou et al.
2010/0069836 A1 3/2010 Satake
2010/0114269 A1 5/2010 Wittenberger et al.
2010/0204560 A1 8/2010 Salahieh et al.
2010/0256629 A1 10/2010 Wylie et al.
2010/0324552 A1 12/2010 Kauphusman et al.
2011/0118632 A1 5/2011 Sinelnikov et al.
2011/0130648 A1 6/2011 Beeckler et al.
2011/0282338 A1 11/2011 Fojtik
2011/0295248 A1 12/2011 Wallace et al.
2011/0301587 A1 12/2011 Deem et al.
2011/0313286 A1 12/2011 Whayne et al.
2012/0019107 A1 1/2012 Gabl et al.
2012/0029511 A1 2/2012 Smith et al.
2012/0065503 A1 3/2012 Rogers et al.
2012/0071870 A1* 3/2012 Salahieh ............ A61B 1/00181 606/33
2012/0079427 A1 3/2012 Carmichael et al.
2012/0101413 A1 4/2012 Beetel et al.
2012/0101538 A1 4/2012 Ballakur et al.
2012/0143177 A1 6/2012 Avitall
2012/0143293 A1 6/2012 Mauch et al.
2012/0191079 A1 7/2012 Moll et al.
2012/0209260 A1 8/2012 Lambert et al.
2013/0085360 A1 4/2013 Grunewald
2013/0090649 A1* 4/2013 Smith ................ A61B 18/1492 606/41
2013/0109982 A1 5/2013 Sato et al.
2013/0150693 A1 6/2013 D'Angelo et al.
2013/0165916 A1 6/2013 Mathur et al.
2013/0165941 A1 6/2013 Murphy
2013/0165990 A1 6/2013 Mathur et al.
2013/0169624 A1 7/2013 Bourier et al.
2013/0261692 A1 10/2013 Cardinal et al.
2013/0274562 A1* 10/2013 Ghaffari ............... A61B 5/6833 601/3
2013/0274658 A1* 10/2013 Steinke .............. A61B 18/1492 606/41
2013/0282084 A1 10/2013 Mathur et al.
2013/0318439 A1 11/2013 Landis et al.
2014/0012242 A1 1/2014 Lee et al.
2014/0018788 A1 1/2014 Engelman et al.
2014/0031813 A1 1/2014 Tellio et al.
2014/0058197 A1 2/2014 Salahieh et al.
2014/0121470 A1 5/2014 Scharf et al.
2014/0148805 A1 5/2014 Stewart et al.
2014/0227437 A1 8/2014 DeBoer et al.
2014/0243821 A1 8/2014 Salahieh et al.
2014/0275993 A1 9/2014 Ballakur
2014/0276756 A1 9/2014 Hill
2014/0276811 A1 9/2014 Koblish et al.
2014/0288546 A1 9/2014 Sherman et al.
2014/0330266 A1 11/2014 Thompson et al.
2014/0357956 A1 12/2014 Salahieh et al.
2015/0005799 A1 1/2015 Lindquist et al.
2015/0025532 A1 1/2015 Hanson et al.
2015/0025533 A1 1/2015 Groff et al.
2015/0057655 A1 2/2015 Osypka
2015/0067512 A1 3/2015 Roswell
2015/0080883 A1 3/2015 Haverkost et al.
2015/0105774 A1 4/2015 Lindquist et al.
2015/0112256 A1* 4/2015 Byrne ............... A61M 25/1029 604/103.02
2015/0112321 A1 4/2015 Cadouri
2015/0119875 A1 4/2015 Fischell et al.
2015/0141982 A1 5/2015 Lee
2015/0157382 A1 6/2015 Avitall et al.
2015/0216591 A1 8/2015 Cao et al.
2015/0216650 A1 8/2015 Shaltis
2015/0265329 A1 9/2015 Lalonde et al.
2015/0265339 A1 9/2015 Lindquist et al.
2015/0265812 A1 9/2015 Lalonde
2015/0272667 A1 10/2015 Govari et al.
2015/0327805 A1 11/2015 Ben-Haim
2015/0341752 A1 11/2015 Flynn
2016/0000499 A1 1/2016 Lennox et al.
2016/0051321 A1 2/2016 Salahieh et al.
2016/0085431 A1 3/2016 Kim et al.
2016/0106499 A1 4/2016 Ogata et al.
2016/0166306 A1 6/2016 Pageard
2016/0175041 A1 6/2016 Govari et al.
2016/0196635 A1 7/2016 Cho et al.
2016/0256305 A1 9/2016 Longo et al.
2016/0374748 A9* 12/2016 Salahieh ............ A61B 18/1492 606/34
2017/0042614 A1 2/2017 Salahieh et al.
2017/0042615 A1 2/2017 Salahieh et al.
2017/0080192 A1 3/2017 Giasolli et al.
2017/0143359 A1 5/2017 Nguyen et al.
2017/0164464 A1 6/2017 Weinkam et al.
2017/0311829 A1* 11/2017 Beeckler ............ A61B 18/1492
2017/0311893 A1 11/2017 Beeckler et al.
2017/0312022 A1 11/2017 Beeckler et al.
2017/0347896 A1 12/2017 Keyes et al.
2017/0348049 A1* 12/2017 Vrba .................. A61B 18/1492
2018/0074693 A1 3/2018 Jones et al.
2018/0110562 A1 4/2018 Govari et al.
2018/0125575 A1 5/2018 Schwartz et al.
2018/0256247 A1 9/2018 Govari et al.
2018/0280080 A1 10/2018 Govari et al.
2018/0333162 A1 11/2018 Saab
2018/0368927 A1 12/2018 Lyons et al.
2019/0059818 A1 2/2019 Herrera et al.
2019/0060622 A1 2/2019 Beeckler
2019/0143079 A1 5/2019 Beeckler et al.
2019/0175262 A1 6/2019 Govari et al.
2019/0175263 A1 6/2019 Altmann et al.
2019/0183567 A1 6/2019 Govari et al.
2019/0201669 A1 7/2019 Govari et al.
2019/0217065 A1 7/2019 Govari et al.
2019/0297441 A1 9/2019 Dehe et al.
2019/0298441 A1 10/2019 Clark et al.
2019/0365451 A1 12/2019 Jung, Jr.
2020/0001054 A1 1/2020 Jimenez et al.
2020/0015693 A1 1/2020 Beeckler et al.
2020/0085497 A1 3/2020 Zhang et al.
2020/0155226 A1 5/2020 Valls et al.
2021/0169567 A1 6/2021 Govari et al.

FOREIGN PATENT DOCUMENTS

CN 102458566 A 5/2012
CN 103118620 A 5/2013
CN 203539434 U 4/2014
CN 104244856 A 12/2014
CN 104546117 A 4/2015
CN 105105844 A 12/2015
CN 105473091 A 4/2016
CN 105473093 A 4/2016
CN 107361840 A 11/2017
EP 0779059 A1 6/1997
EP 1790304 A2 5/2007
EP 2749214 A1 7/2014
EP 2865350 A2 4/2015
EP 2875790 A2 5/2015
EP 3238646 A2 11/2017
EP 3238648 A1 11/2017
EP 3251622 A1 12/2017
EP 3300680 A1 4/2018
EP 3315087 A1 5/2018
EP 3332727 A2 6/2018
EP 3571983 A2 11/2019
EP 3586778 A1 1/2020
EP 3653153 A1 5/2020
JP H06261951 A 9/1994

(56) References Cited

FOREIGN PATENT DOCUMENTS

| | | | | |
|---|---|---|---|---|
| JP | H1176233 A | 3/1999 | | |
| JP | 2000504242 A | 4/2000 | | |
| JP | 2002538932 A | 11/2002 | | |
| JP | 2005052424 A | 3/2005 | | |
| JP | 2010501319 A | 1/2010 | | |
| JP | 2010507404 A | 3/2010 | | |
| JP | 2012024156 A | 2/2012 | | |
| JP | 2013013726 A | 1/2013 | | |
| JP | 2013078587 A | 5/2013 | | |
| JP | 2013529109 A | 7/2013 | | |
| JP | 2014529419 A | 11/2014 | | |
| JP | 2015503365 A | 2/2015 | | |
| JP | 2015100706 A | 6/2015 | | |
| JP | 2015112113 A | 6/2015 | | |
| JP | 2015112114 A | 6/2015 | | |
| JP | 2015518776 A | 7/2015 | | |
| JP | 2016515442 A | 5/2016 | | |
| JP | 2016116863 A | 6/2016 | | |
| JP | 2017202306 A | 11/2017 | | |
| WO | 0056237 A2 | 9/2000 | | |
| WO | 02102231 A2 | 12/2002 | | |
| WO | 2005041748 A2 | 5/2005 | | |
| WO | 2008049087 A2 | 4/2008 | | |
| WO | 2011143468 A2 | 11/2011 | | |
| WO | 2013049601 A2 | 4/2013 | | |
| WO | 2013052919 A2 | 4/2013 | | |
| WO | 2013154776 A2 | 10/2013 | | |
| WO | 2014/168987 A1 | 10/2014 | | |
| WO | 2015049784 A1 | 4/2015 | | |
| WO | 2016183337 A2 | 11/2016 | | |
| WO | 2016210437 A1 | 12/2016 | | |
| WO | 2017024306 A1 | 2/2017 | | |
| WO | WO-2017087549 A1 * | 5/2017 | .......... | A61B 1/0684 |
| WO | 2018106569 A1 | 6/2018 | | |
| WO | 2018129133 A1 | 7/2018 | | |
| WO | 2019095020 A1 | 5/2019 | | |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.

International Search Report and Written Opinion for International Application No. PCT/IB2019/052313, mailed Jul. 22, 2019, 8 Pages.

International Search Report and Written Opinion for International Application No. PCT/IB2019/056381, mailed Dec. 17, 2019, 10 pages.

International Search Report and Written Opinion for International Application No. PCT/IB2019/057743, mailed Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 mailed Sep. 13, 2017, 13 Pages.

Partial European Search Report for European Application No. 17205876.0, mailed Feb. 22, 2018, 10 Pages.

Reddy V.Y., et al., "Balloon Catheter Ablation to Treat Paroxysmal Atrial Fibrillation: What is the Level of Pulmonary Venous Isolation? ," Heart Rhythm, Mar. 2008, vol. 5, No. 3, pp. 353-360, 3 Pages.

Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QKMWJME].

Youtube: "New Interface TactiCath Contact Force Ablation Catheter," Nov. 26, 2013, 1 Pages, [Retrieved on Nov. 19, 2020], Retrieved from URL: https: /Awww.youtube.com/watch?v= aYvYO8Hpylg].

Exam Report dated Dec. 19, 2023, from corresponding European Application No. 19209784.8.

Search Report with English translation dated Jun. 14, 2023, from corresponding Japanese Application No. 2019-207679.

(56) References Cited

OTHER PUBLICATIONS

Notice of Reasons for Refusal with English translation dated Jun. 20, 2023, from corresponding Japanese Application No. 2019-207679.
Written Opinion with English translation dated Sep. 20, 2023, from corresponding Japanese Application No. 2019-207679.
Decision to Grant a Patent with English translation dated Sep. 26, 2023, from corresponding Japanese Application No. 2019-207679.
First Search dated Dec. 13, 2023, from corresponding Chinese Application No. 201911134721.0.
First Office Action dated Dec. 13, 2023, from corresponding Chinese Application No. 201911134721.0.
Supplemental Search dated Apr. 3, 2024, from corresponding Chinese Application No. 201911134721.0.
Notification to Grant Patent Right for Invention with English translation dated Jul. 22, 2024, from corresponding Chinese Application No. 201911134721.0, 7 pages.

* cited by examiner

MEDICAL PROBE WITH WIRING DISPOSED BETWEEN TWO EXPANDABLE MEMBRANES

CROSS-REFERENCE TO RELATED APPLICATIONS

The present application is a continuation application of U.S. patent application Ser. No. 16/657,319, filed Oct. 18, 2019, granted on Aug. 8, 2023 as U.S. Pat. No. 11,717,344, which claims the benefit of priority under 35 U.S.C. § 119 to prior filed U.S. Provisional Patent Application No. 62/769,424 filed on Nov. 19, 2018, the entire contents of each of which is incorporated herein by reference in its entirety as if fully set forth herein.

BACKGROUND

Ablation of cardiac tissue has been used to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters may be visualized using fluoroscopy.

SUMMARY OF THE DISCLOSURE

In the manufacturing of a medical probe having a balloon and electrodes arrayed on the balloon, we have determined that the electrical connection between a thermocouple (i.e., temperature sensor) on each electrode may not be optimal when the thermocouple/electrode is connected to wires that extends from inside the balloon due to the number of wires (referenced also as a "bifilar") connecting to the ten or more electrodes on the balloon. Accordingly, applicant has devised an electrophysiology catheter having a balloon with three expandable membranes attached to each other such that the wires no longer extend from inside the first membrane yet at the same time is captured between the first membrane and a second membrane.

Specifically, we have devised an electrophysiology probe that includes a tubular member, a first expandable membrane, a second expandable membrane, a plurality of electrodes with a plurality of wires connected to the electrodes. The tubular member extends along a longitudinal axis from a first end to a second end with a first expandable membrane having an outer surface and an inner surface disposed about the longitudinal axis. The first expandable membrane has a first expandable membrane portion being coupled to the second end of the tubular member and second expandable membrane portion spaced apart from the first expandable membrane portion along the longitudinal axis. The first expandable membrane is configured to be expanded from a compressed shape to a balloon shaped member. The plurality of electrodes are disposed on the outer surface of the first expandable membrane with one or more wires connected to each of the plurality of electrodes. Each wire extends from the tubular member to the electrode. The second expandable membrane encapsulates the one or more wires between the second expandable membrane and the first expandable membrane so that the wires are constrained between the first and second expandable membrane with the electrodes exposed to ambient environment.

The probe is also configured to have the following features, which can be combined into various combinations or permutations, such as, for example, the tubular member defines a first lumen that extend from the first end to the second end so that the wires are contained in the first lumen; the tubular member defines a second lumen that extends through the first expandable membrane to allow for another instrument to pass through the second lumen; the tubular member defines a third lumen that extends to a portion within the first expandable membrane, the third lumen configured to allow irrigation fluid to be delivered to the portion within the first expandable membrane; the first expandable membrane includes a plurality of openings that extends through the membrane to allow for irrigation fluid to flow from inside the membrane to outside of the membrane; the electrodes extend from a central electrode portion equiangularly about the longitudinal axis from the first expandable membrane portion towards the second expandable membrane portion such that the second expandable membrane encapsulates a portion of each of the electrodes proximate the second expandable membrane portion; wherein each of the plurality of electrodes defines a fishbone pattern not covered by the second expandable membrane; each electrode is coupled to the outer surface of the first expandable membrane via a substrate; a radiopaque marker is defined by a fish-head portion of each electrode; each electrode includes a radiopaque marker having a configuration different from other radiopaque markers on the other electrodes; a third expandable membrane disposed proximate the first expandable membrane portion so that the third expandable membrane encircles a portion of the first expandable membrane about the longitudinal axis; the third expandable membrane encapsulates a portion of a substrate for each of the plurality of electrodes between the first expandable membrane and the third expandable membrane; a retaining ring disposed about the third expandable membrane; the first expandable membrane includes a circumferential surface area of approximately 52% of a total surface area of the first expandable membrane that is not covered by the second and third expandable membranes; each substrate for each electrode includes a substrate surface area approximately 8 percent of the exposed outer circumferential surface area of the first expandable membrane; the plurality of electrodes comprises ten electrodes disposed equiangularly about the longitudinal axis on the first membrane; the second expandable membrane and third expandable membrane cover approximately half of the outer surface area of the first expandable membrane; the first expandable membrane includes a generally spheroidal member with a diameter as referenced to the longitudinal axis of about 30 millimeters and wherein the second expandable membrane and the third expandable membrane each includes a hemi-spherical member; or the first expandable membrane includes a first configuration disposed in a tubular member of less than 8 French and a second configuration disposed outside the tubular member of about 30 millimeters as referenced to the longitudinal axis.

BRIEF DESCRIPTION OF THE DRAWINGS

While the specification concludes with the claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Ablation of cardiac tissue to correct a malfunctioning heart is a well-known procedure for implementing such a correction. Typically, to successfully ablate, cardiac electro potentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation. The medical probe used in the ablation procedure are therefore known as an electrophysiology probe. Such probe may have a handle connected to a mapping and diagnostic system, which can be understood from commonly owned U.S. patent application Ser. No. 15/939,154 filed on Mar. 28, 2018 entitled IRRIGATED ELECTROPHYSIOLOGY CATHETER WITH DISTINGUISHABLE ELECTRODES FOR MULTI-ELECTRODE IDENTIFICATION AND ORIENTATION UNDER 2-D VISUALIZATION, which is hereby incorporated by reference with a copy attached to the Appendix.

Figure 1:
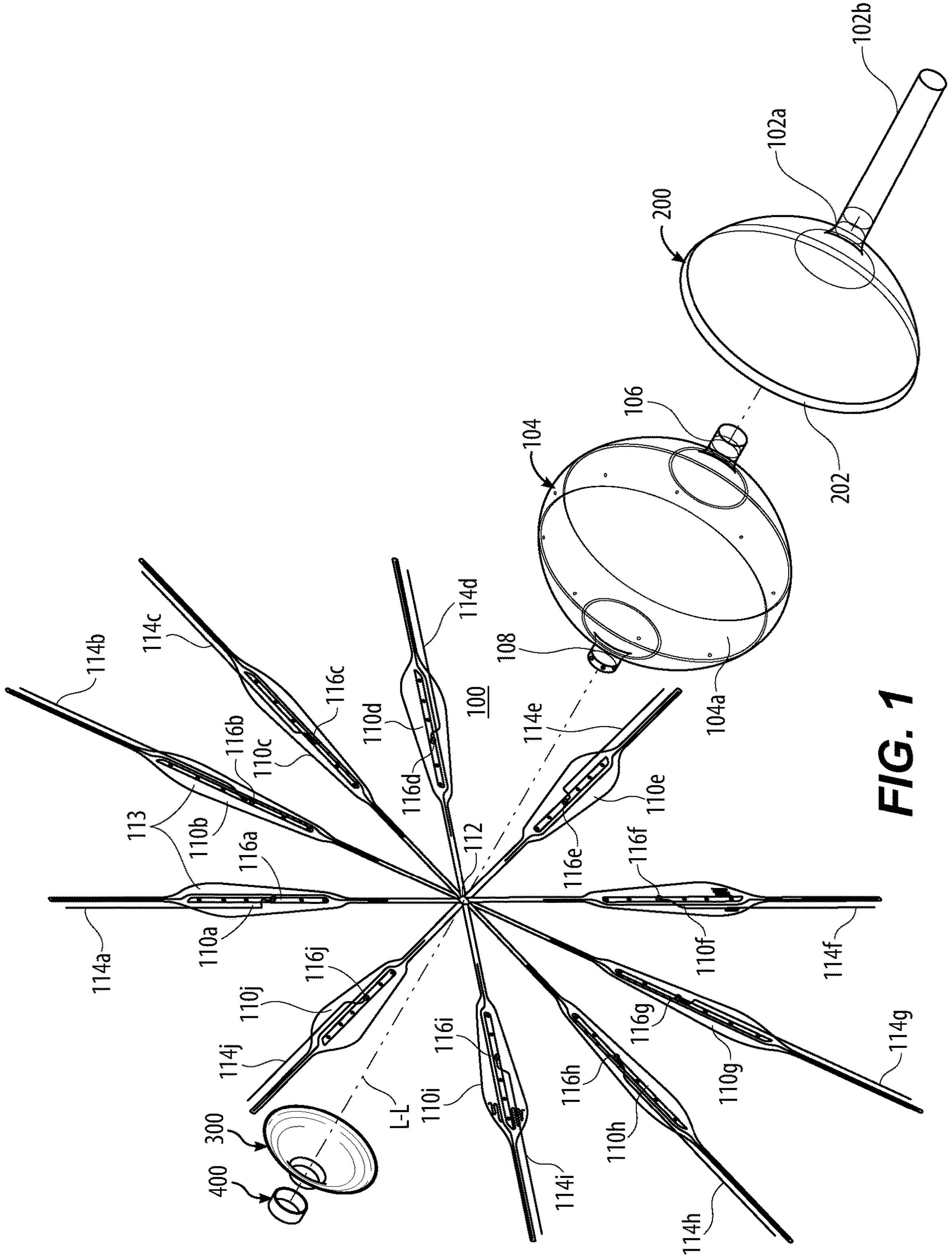
FIG. 1 is an exploded perspective view of the medical probe which shows a base balloon or first expandable membrane with radiating electrode assemblies that are partially covered by respective second and third expandable membranes.

FIG. 1 illustrates an exploded perspective view of an electrophysiology probe 100 that includes a tubular member 102 extending along a longitudinal axis L-L from a first (proximal) end 102*b* to a second (or distal) end 102*a*. A first expandable membrane 104 is attached to the tubular member 102 near the distal end 102*b*. The membrane 104 has an outer surface 104*a* and an inner surface 104*b* disposed about the longitudinal axis L-L. The outer surface 104*a* is exposed to the ambient environment while the inner surface 104*b* is exposed to the internal volume of the balloon defined by the membrane 104. The first expandable membrane 104 has a first expandable distal membrane portion 108 being coupled to the second end 102*a* of the tubular member 102 and second expandable distal membrane portion 106 spaced apart from the first expandable distal membrane portion 108 along the longitudinal axis L-L.

It is noted that first expandable membrane 104 is configured to be expanded from a compressed shape (generally tubular configuration) to a balloon (or generally spheroidal) shaped member. A plurality of electrodes (110*a*, 110*b*, 110*c*, 110*d*, 110*e*, 110*f*, 110*g*, 110*h*, 110*i* and 110*j*, which may be referred to singularly or collectively as "electrode 110") are disposed on the outer surface 104*a* of the first expandable membrane 104. The electrodes 110 are arranged so that they radiate from a generally common center or centroid substrate 112 near the second expandable distal membrane portion 108 which is distal to the tubular member 102. The electrodes 110*a*-110*j* may have one or more wires, i.e., bifilar 114*a*-114*j*, respectively, connected to each of the plurality of electrodes 110*a*-110*j* via a connection junction 116*a*-116*j*. Each of the wires 114*a*-114*j* (which may be singular in form "wire" or plural "wires" will be collectively referred to as "wire 114") is connected to the connection point at the "underside" surface of the electrode 110. The underside surface of each electrode 110 is the electrode surface that is not exposed to the ambient environment and is typically bonded to the outer surface 104*a* of the membrane 104. As the connection point 116 (typically a solder point) is generally at the center of the electrode, the wire is covered by the underside surface of each electrode. However, as each wire or bifilar 114*a*-114*j* extends toward the tubular member 102, the electrode surface or the substrate on which the electrode is bonded thereto becomes smaller thereby leaving the wire or bifilars 114*a*-114*j* exposed.

Figure 2:
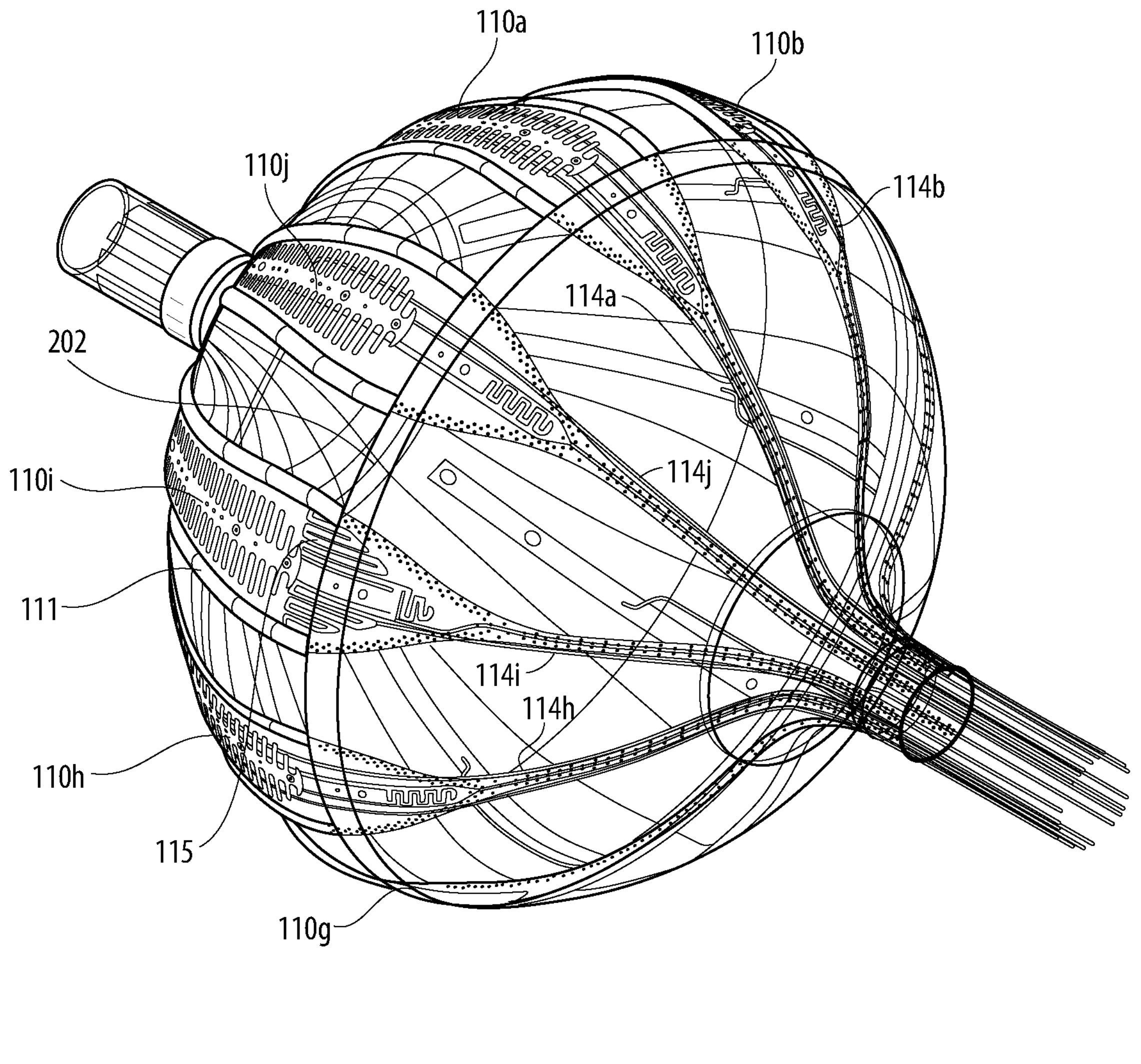
FIG. 2 illustrates an assembled medical probe of FIG. 1.
Figure 3A:
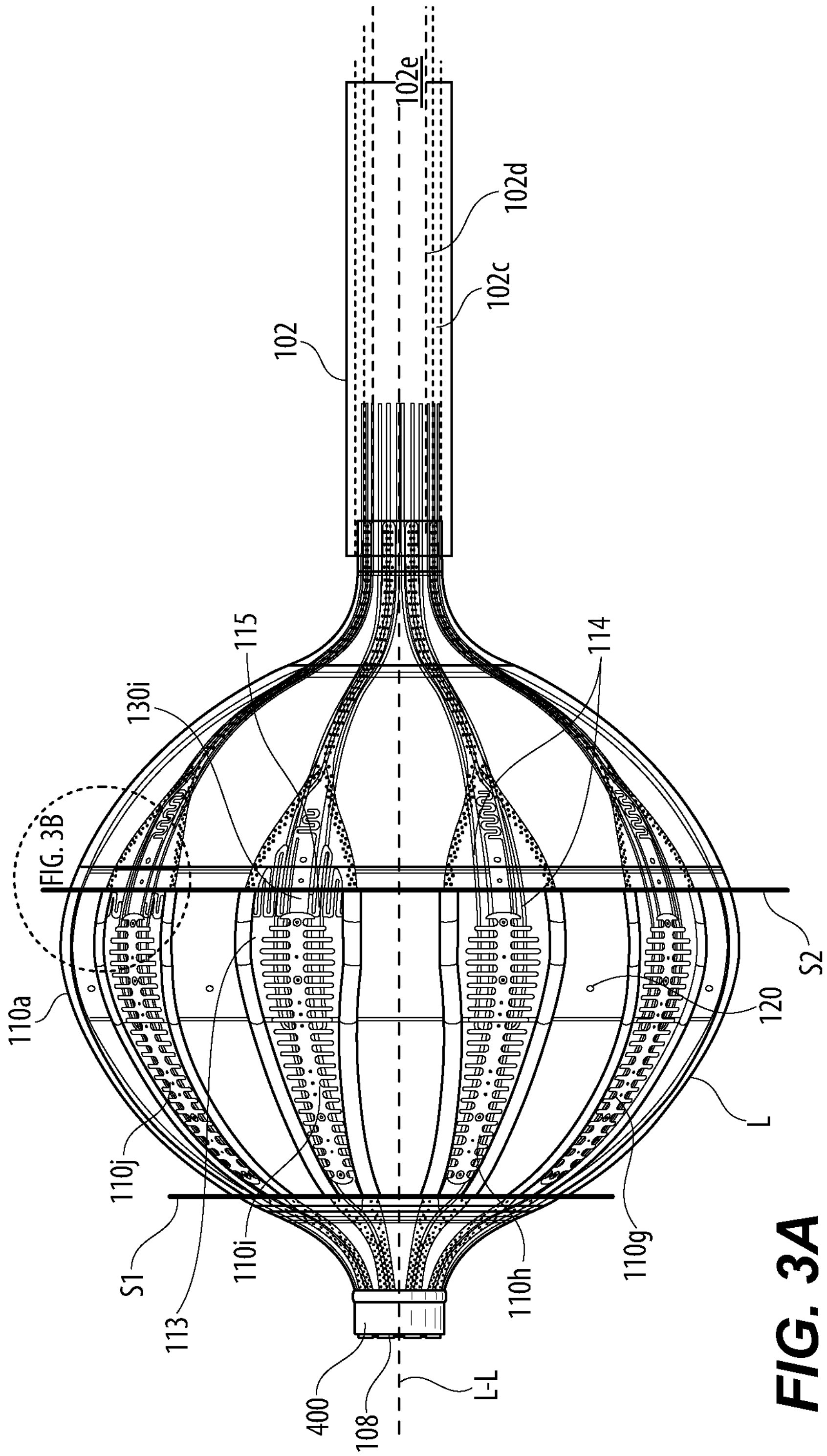
FIG. 3A is a side view of the medical probe of FIG. 2.
Figure 3B:
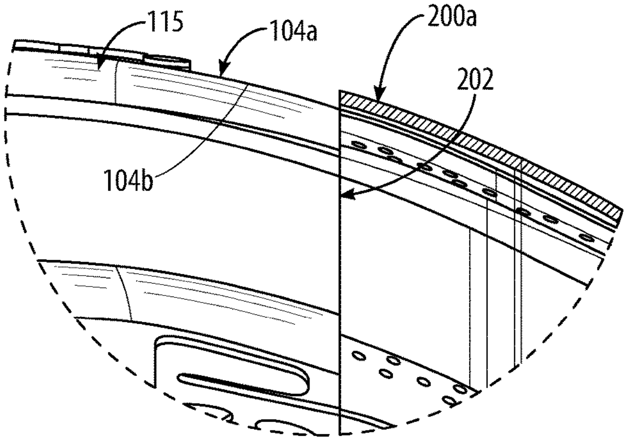
FIG. 3B is a blown-up side view of a portion of the membrane of FIG. 3A.
Figure 4:
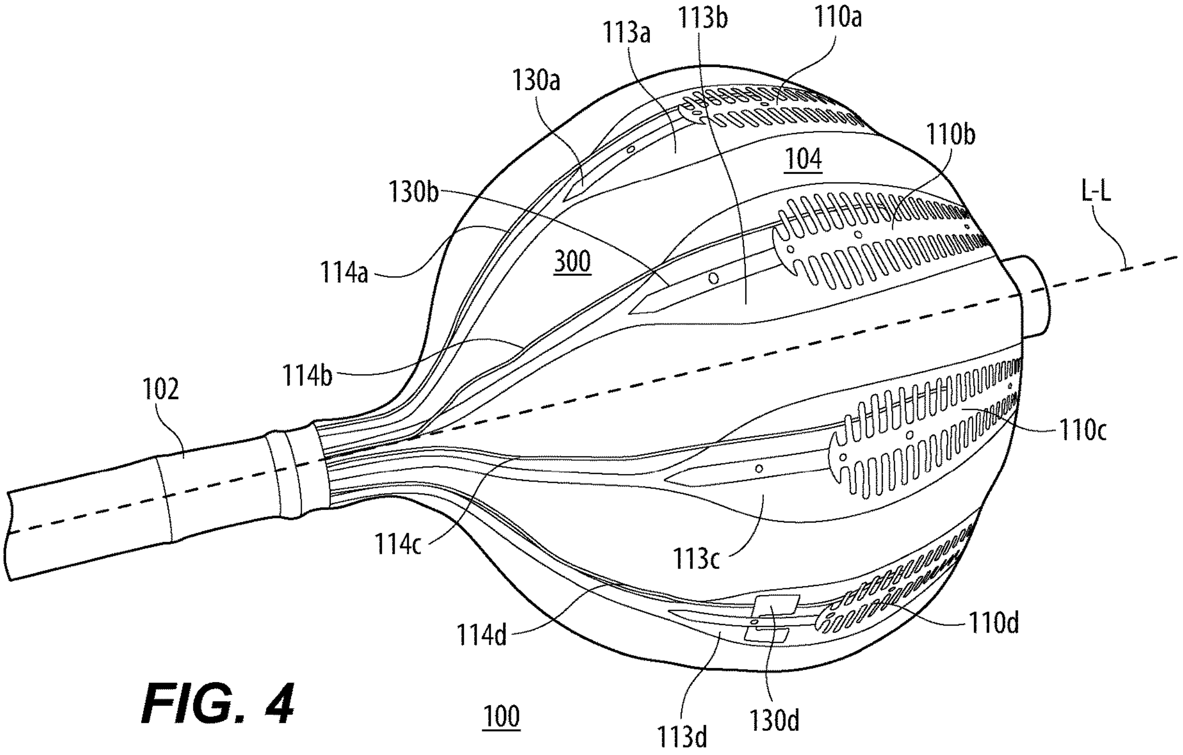
FIG. 4 is a photograph of an actual prototype according to an embodiment described and illustrated herein.

As can be seen in FIG. 2, when group of wires 114*a*-114*j* are mounted on the membrane 104, each wire 114 is configured to extend from the tubular member 102 to the respective electrode 110 such that each wire follows the topographic outer surface 104*a* of membrane 104. In extending the wires 114 toward the tubular member 102, the wires 114 become exposed to the ambient environment (e.g., biological tissues or blood) as each wire 114 leaves the underside surface of each electrode or the underside surface of the substrate 113 (FIG. 3A). As each wire 114 may be used to conduct or transmit electrical energy or signals, it would be detrimental to expose the wires 114 to the ambient biological tissue environment. As such, we have devised a second expandable membrane 200 that encapsulates the one or more wires (114*a*-114*j*) between the second expandable membrane 200 and the first expandable membrane 104 so that the wires 114*a*-114*j* are constrained between the first and second expandable membrane (FIG. 4). Such configuration eliminates the exposure of the wires to the ambient environment yet still allowing the electrodes/thermocouples to be exposed to biological tissues so that the electrodes and thermocouples to work for their intended purposes. Moreover, as the wires 114 are constrained or captured between the first and second membranes, there is virtually no likelihood of the wires being entangled or mis-connected to the wrong electrode or thermocouple during assembly. In the preferred embodiment, each wire of the bifilar is coupled to a temperature sensor in the form of a thermocouple 116 disposed on or near each electrode 110.

It is noted that tubular member 102 defines a first internal passageway in the form of a lumen 102*c*, shown here as dashed lines in FIG. 3A, that extends from the first end 102*a* to the second end 102*b* of tubular member 102 so that the one or more wires are disposed in the first lumen 102*c*. To allow other instruments (e.g., guide wires, optical sensor etc.,) to be delivered through the balloon 104 (and outside of the distal-most portion 108 of balloon) the tubular member 102 can be provided with a second lumen 102*d* that extends through the membrane portions 106 and 108 to allow for another instrument to pass through the second lumen 102*d*. Additionally, the tubular member 102 can be provided with yet another internal passageway in the form of a third lumen 102*e*. Irrigation fluid can be provided in either of the second lumen 102*d* or third lumen 102*e* so that the irrigation fluid flows into the internal volume of the membrane 104, through openings or pores 120 provided through the membrane inner surface 104*b* and outer surface 104*a* to outside of the membrane 104 to the ambient environment (e.g., biological tissues or organ). Each electrode may have four irrigation openings formed on the electrode such that the electrode irrigation openings are aligned with the pores 120 of the membrane. In the preferred embodiment, lumen 102*c*, lumen 102*d* and 102*e* are configured or extruded as concentric passageways, in the form of a tube 102*e* within tube 102*d* within a tube 102*c* with outer tubular member 102. Tubular member 102 can be a suitable biocompatible polymer as is known to those skilled in the art.

Referring to FIG. 2, the plurality of electrodes 110*a*-110*j* extend from a substrate centroid 112 equiangularly about the longitudinal axis L-L from the first expandable distal membrane portion 108 towards the second expandable distal membrane portion 106 such that the second expandable membrane 200 encapsulates a portion of each of the electrodes (110*a*-110*j*) proximate the second expandable membrane portion 106. The second expandable membrane 200 has a border 202 (FIG. 1) that extends over a proximal portion (i.e., fish-head 115) of the electrode 110 outer surface (FIG. 2) while allowing the electrode fish-bone pattern 110 to be exposed to the ambient environment.

That is, each of the plurality of electrodes 110*a*-110*j* defines a fishbone pattern not covered by the second expandable membrane 200 to allow the fishbone electrodes to be exposed to the ambient environment. Each electrode (110*a*-110*j*) is coupled to the outer surface of the first expandable membrane 104 via a substrate 113 which itself is connected to or bonded to the outer surface 104*a* of the first expandable membrane 104. The electrode 110*a*-110*j* can have a portion of its perimeter bonded directly to membrane 104. A suitable seal 111 can be formed so that the seal 111 runs along the outer perimeter of the substrate 113 of each electrode (110*a*-110*j*). In a preferred embodiment, the seal 111 can be provided in the form of a polyurethane seal.

Referring to FIG. 3A, a radiopaque marker 130 is defined by a proximal fish-head portion of each electrode such that there can be respective radiopaque markers 130*a*, 130*b*, 130*c*, 130*d*, 130*e*, 130*f*, 130*g*, 130*h*, 130*i* and 130*j* for corresponding electrodes 110*a*-110*j*. To ensure that the location of each electrode can be determined while inside a body organ with x-rays, each electrode 110 may have a radiopaque marker (130*a*-130*j*) with each marker having a configuration different from other radiopaque markers on the other electrodes.

Referring to FIG. 1, a third expandable membrane 300 can be disposed proximate the first expandable distal membrane portion 108 so that the third expandable membrane 300 encircles an outer surface portion of the first expandable membrane 104 about the longitudinal axis L-L proximate the distal portion 108 of the membrane 104. The third expandable membrane encapsulates a portion of the substrate 113 (FIG. 3A) for each of the plurality of electrodes near distal portion 108 of membrane 104. Preferably, the third expandable membrane 300 allows for encapsulation of the substrates 113 of each electrode (110*a*-110*j*) as the substrates 113 converge to centroid 112 near the distal portion 108 of the membrane 104. A retaining ring 400 is disposed about the third expandable membrane 300 (near distal portion 108 of membrane 104) to hold the third expandable membrane 300 as well as the substrates 113 to the first expandable membrane 104. The third expandable membrane 300 can be bonded to the first expandable membrane 104 thereby capturing the substrate 113 therebetween the two membranes (104 and 300).

Figure 3C:
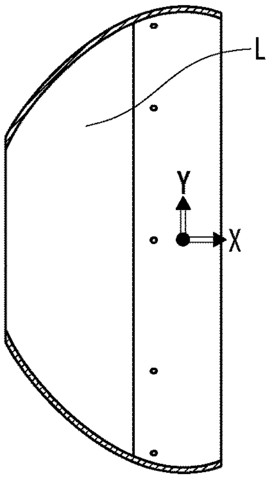
FIG. 3C illustrates a lateral or circumferential surface area (shaded portion) not covered by the hemispherical second and third expandable membranes of FIG. 1.

Referring to FIG. 3A, it is noted that the surface area of the membrane 104 that is exposed (i.e., not covered) by second expandable membrane 200*a* and third expandable membrane has a circumferential surface area L delineated between a virtual slice S1 (defined by the intersection of third expandable membrane 300 with first expandable membrane 104) orthogonal to axis L-L and virtual slice S2 orthogonal to the longitudinal axis L-L whereby slice S2 is defined by the intersection of the second expandable membrane 200 to the first expandable membrane 104. For clarity, it can be seen in FIG. 3C that if the first expandable membrane 104 approximates a sphere (when membrane 104 is expanded to its service characteristic) then the circumferential surface area L can be determined once the parameters of the spheroid body is known. In the preferred embodiment, shown in FIG. 4, the first expandable membrane 104 includes a circumferential surface area L (FIGS. 3A and 3C) of approximately 52% of a total surface area of the first expandable membrane 104. That is, the circumferential surface area L is the exposed surface area (without any electrode or substrate) of first expandable membrane 104 or outer circumferential area of first expandable membrane 104 that is also not covered by the second expandable membrane 200*a* and third expandable membrane 300. Further, it is noted that each substrate 113 for each electrode 110 includes a substrate surface area approximately 8% of the exposed outer circumferential surface area L of the first expandable membrane 104. In the preferred embodiments, the second expandable membrane 200, 200*a* and third expandable membrane 300 cover approximately half of the outer surface area of the first expandable membrane 104.

In the preferred embodiments, the first expandable membrane includes a generally spheroidal member with a diameter as referenced to the longitudinal axis L-L of about 30 millimeters and the second expandable membrane and the third expandable membrane each includes a hemi-spherical member with the respective major diameter of each hemi-spherical member being less than 30 mm. In the preferred embodiments, the total surface area of membrane 104 is about 4500 squared-mm while the circumferential surface area L is about 2400 squared-mm and each flexible substrate 113 is about 200 squared-mm when the membrane 104 is at its fully expanded (i.e., designed) configuration, shown exemplarily in FIG. 4.

The balloon 104 of the diagnostic/therapeutic catheter has an exterior wall or membrane 104*a* of a bio-compatible material, for example, formed from a plastic such as polyethylene terephthalate (PET), polyurethane or PEBAX®. The tubular shaft 102 and the distal shaft end 102*a* define a longitudinal axis L-L of the balloon 104. The balloon 104 is deployed, in a collapsed configuration as described in commonly-owned U.S. patent application Ser. No. 15/939,154 filed on Mar. 28, 2018 (via the lumen 23 of the probe 20 in this prior application, which is incorporated by reference herein to this present application). The membrane 104*a* of the balloon 104 is formed with irrigation pores or apertures 120 (shown in FIG. 3A) through which the fluid (e.g., saline) can exit from the interior of the balloon 104 to outside the balloon for cooling the tissue ablation site at the ostium.

As described earlier in relation to FIG. 2, membrane 24 supports and carries a combined electrode and temperature sensing member which is constructed as a multi-layer flexible circuit electrode assembly 110*a*-110*j*. The "flex circuit electrode assembly" 110*a*-110*j* may have many different geometric configurations than as shown here. In the illustrated embodiment, the flex circuit electrode assembly 110*a*-110*j* has a plurality of radiating substrates or strips 113*a*-113*j*, as best seen in FIG. 1. The substrates 113*a*-113*j* are evenly distributed about the distal end 108 and the balloon 104. Each substrate 113*a*-113*j* has wider proximal portion that gradually tapers to a narrower distal portion as referenced to the longitudinal axis.

For simplicity, the flex circuit electrode assembly 110 is described with respect to one of its substrate 113 as shown in FIG. 3A, although it is understood that following description may apply to each substrate 113 of the assembly 110. The flex circuit electrode assembly 110 includes a flexible and resilient sheet substrate material 113, constructed of suitable bio-compatible materials, for example, polyimide. In some embodiments, the sheet substrate material 113 has a greater heat resistance (or a higher melting temperature) compared to that of the balloon membrane 104. In some embodiments, the substrate material 113 is constructed of a thermoset material having a decomposition temperature that is higher than the melting temperature of the balloon membrane 104 by approximately 100 degrees Celsius or more.

The substrate material 113 is formed with one or more irrigation pores or apertures (not labeled) that are in alignment with the irrigation apertures 120 of the balloon member 104 so that fluid passing through the irrigation apertures 120 and (not labeled) can pass to the ablation site on the ostium.

The substrate material 113 has a first or outer surface facing away from the balloon membrane 104, and a second or inner surface facing the balloon membrane 104. On its outer surface, the substrate material 113 supports and carries the contact electrodes 110. The configuration or trace of the contact electrode 110 may resemble a "fishbone" but it should be noted that the invention is not limited to such configuration. In contrast to an area or "patch" ablation electrode, the fingers of the contact electrode 110 advantageously increase the circumferential or equatorial contact surface of the contact electrode 110 with the ostium while void regions between adjacent fingers advantageously allow the balloon 104 to collapse inwardly or expand radially as needed at locations along its equator. In the illustrated embodiment, the fingers have different lengths, some being longer, others being shorter. For example, the plurality of fingers includes a distal finger, a proximal finger and fingers therebetween, where each of the fingers in between has a shorter adjacent finger. For example, each finger has a length different from its distal or proximal immediately adjacent neighboring finger(s) such that the length of each finger generally follows the tapered configuration of each substrate 113. In the illustrated embodiment, there are 22 fingers extending across (past each lateral side of) the elongated portion. In some embodiments, the contact electrode 110 includes gold with a seed layer between the gold and the membrane 104. The seed layer may include titanium, tungsten, palladium, silver, or combinations thereof.

Figure 5:
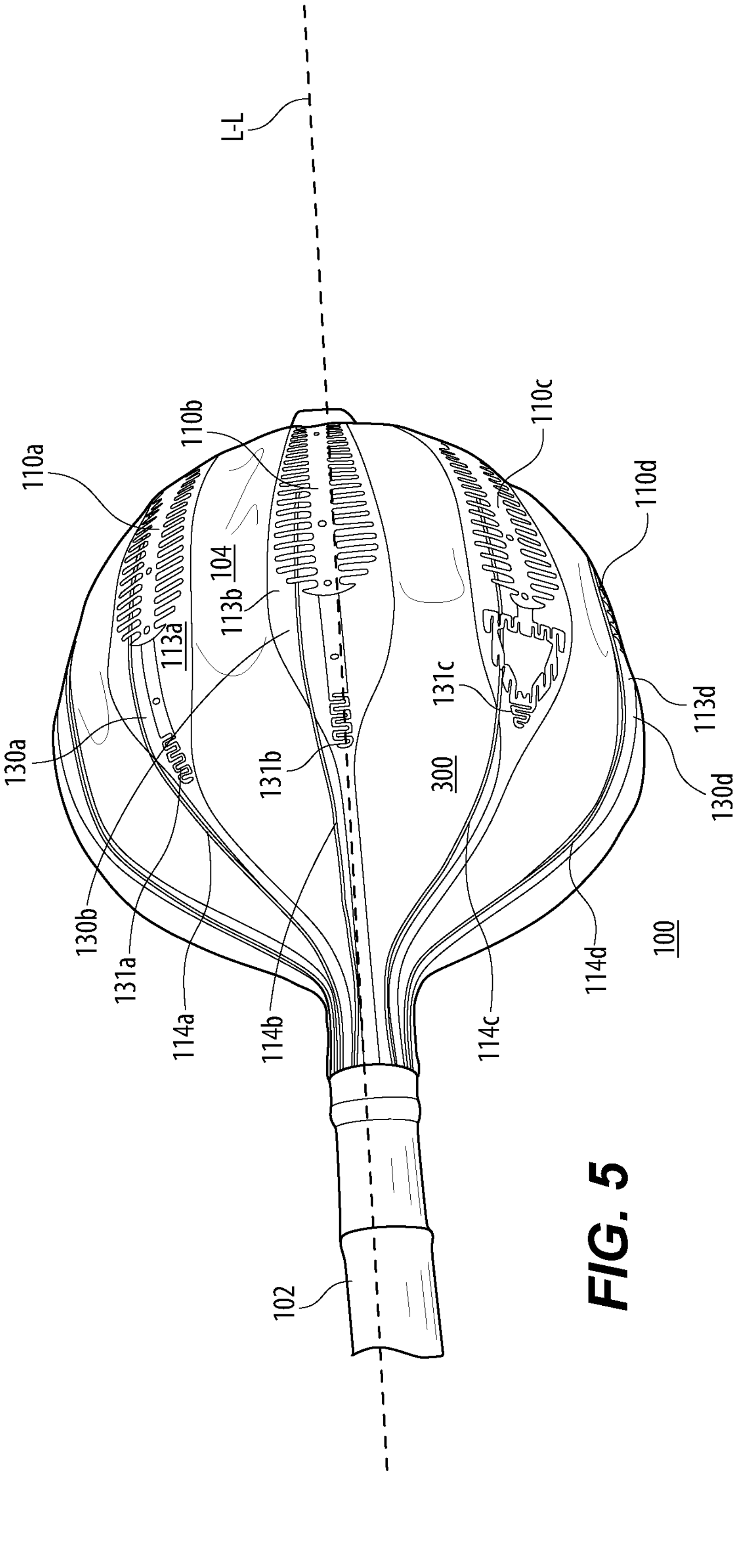
FIG. 5 is a photograph of yet another prototype of the embodiments described and illustrated herein.

As shown in FIG. 5, the flexible electrode may have its radiopaque marker in the variation identified as 131*a*, 131*b*, 131*c* and so on to assist in the identification of the electrode being energized. The markers 131*a*-131*j* have various serpentine configurations (as compared to FIG. 4) to allow for increased flexibility due to the presence of the second membrane 200 which tend to reduce the flexibility of the device near the markers 131*a*-131*j*.

Description of the diagnostic/therapeutic catheter in accordance with the foregoing disclosure may be found in U.S. patent application Ser. No. 15/360,966, published as U.S. Patent Application Publication No. 2017/0312022, which is incorporated by reference herein in its entirety and attached hereto this application in the Appendix.

Any of the examples or embodiments described herein may include various other features in addition to or in lieu of those described above. The teachings, expressions, embodiments, examples, etc. described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but, in any order, if the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. An electrophysiology probe comprising:

a first expandable membrane having an outer surface disposed about a longitudinal axis, the first expandable membrane having a first expandable membrane portion and a second expandable membrane portion spaced apart from the first expandable membrane portion along the longitudinal axis;

a plurality of electrodes disposed on the outer surface of the first expandable membrane, each comprising a substrate;

one or more wires extending from each of the plurality of electrodes;

a second expandable membrane that encapsulates the one or more wires between the second expandable membrane and the first expandable membrane, the one or more wires being in direct contact with the second expandable membrane; and a third expandable membrane disposed proximate the first expandable membrane portion so that the third expandable membrane at least partially encircles the first expandable membrane about the longitudinal axis, wherein the third expandable membrane encapsulates a portion of the substrate for each of the plurality of electrodes between the first expandable membrane and the third expandable membrane, wherein the third expandable membrane is spaced apart from the second expandable membrane along the longitudinal axis.

2. The electrophysiology probe of claim 1, wherein a tubular member defines a lumen that extends from a first end to a second end so that the one or more wires are contained in the lumen.

3. The electrophysiology probe of claim 1, wherein a tubular member defines a lumen that extends through the first expandable membrane to allow for another instrument to pass through the lumen.

4. The electrophysiology probe of claim 1, wherein a tubular member defines a lumen that extends to a portion within the first expandable membrane, the lumen configured to allow irrigation fluid to be delivered to the portion within the first expandable membrane.

5. The electrophysiology probe of claim 1, wherein the first expandable membrane includes a plurality of openings that extends through the first expandable membrane to allow for irrigation fluid to flow from inside the first expandable membrane to outside of the first expandable membrane.

6. The electrophysiology probe of claim 1, wherein the plurality of electrodes extend from a central electrode portion equiangularly about the longitudinal axis from the first expandable membrane portion towards the second expandable membrane portion such that the second expandable membrane encapsulates a portion of each of the plurality of electrodes proximate the second expandable membrane portion.

7. The electrophysiology probe of claim 1, wherein each of the plurality of electrodes defines a fishbone pattern not covered by the second expandable membrane.

8. The electrophysiology probe of claim 1, wherein each of the plurality of electrodes is coupled to the outer surface of the first expandable membrane via the substrate.

9. The electrophysiology probe of claim 1, wherein a radiopaque marker is defined by a fish-head portion of each of the plurality of electrodes.

10. The electrophysiology probe of claim 1, wherein each of the plurality of electrodes includes a radiopaque marker having a configuration different from the radiopaque marker on others of the plurality of electrodes.

11. The electrophysiology probe of claim 1, further comprising a retaining ring disposed about the third expandable membrane.

12. The electrophysiology probe of claim 1, wherein the first expandable membrane includes a circumferential surface area of approximately 52% of a total surface area of the first expandable membrane that is not covered by the second and third expandable membranes.

13. The electrophysiology probe of claim 1, wherein the substrate for each of the plurality of electrodes includes a substrate surface area approximately 8% of an exposed outer circumferential surface area of the first expandable membrane.

14. The electrophysiology probe of claim 1, wherein the plurality of electrodes comprises ten electrodes disposed equiangularly about the longitudinal axis on the first expandable membrane.

15. The electrophysiology probe of claim 1, wherein the second expandable membrane and the third expandable membrane cover approximately half of an area of the outer surface of the first expandable membrane.

16. The electrophysiology probe of claim 1, wherein the first expandable membrane includes a generally spheroidal member with a diameter as referenced to the longitudinal axis of about 30 millimeters and wherein the second expandable membrane and the third expandable membrane each includes a hemi-spherical member.

17. The electrophysiology probe of claim 1, wherein the first expandable membrane includes a first configuration configured to be disposed in a tubular member, the first expandable membrane having an inner diameter of less than 8 French in the first configuration, and a second configuration disposed outside the tubular member, the first expandable membrane having a dimension of about 30 millimeters in the second configuration as referenced to the longitudinal axis.

* * * * *